(12) United States Patent
Tuo et al.

(10) Patent No.: US 11,272,711 B2
(45) Date of Patent: Mar. 15, 2022

(54) ANTIMICROBIAL AND SYNERGISTIC PHYTOCHEMICAL COMPOSITION, ITS PREPARATION AND APPLICATIONS

(71) Applicant: Purpana (Beijing) Technologies Co., Ltd., Beijing (CN)

(72) Inventors: Daisong Tuo, Beijing (CN); Fukang Zhan, Beijing (CN); Xinyuan Xu, Beijing (CN); Liquan Sun, Beijing (CN); Chen Zou, Beijing (CN); Dan Zhu, Beijing (CN)

(73) Assignee: PURPANA (BEIJING) TECHNOLOGIES CO., LTD., Beijing (CN)

( * ) Notice: Subject to any disclaimer, the term of this patent is extended or adjusted under 35 U.S.C. 154(b) by 654 days.

(21) Appl. No.: 15/763,390

(22) PCT Filed: Sep. 28, 2016

(86) PCT No.: PCT/CN2016/100604
§ 371 (c)(1),
(2) Date: Mar. 26, 2018

(87) PCT Pub. No.: WO2017/063504
PCT Pub. Date: Apr. 20, 2017

(65) Prior Publication Data
US 2018/0235238 A1 Aug. 23, 2018

(30) Foreign Application Priority Data

Oct. 14, 2015 (CN) .......................... 201510661990.8

(51) Int. Cl.
| | | |
|---|---|---|
| *A01N 65/30* | (2009.01) | |
| *A01N 65/20* | (2009.01) | |
| *A01N 43/22* | (2006.01) | |
| *A01N 65/08* | (2009.01) | |
| *A61K 36/48* | (2006.01) | |
| *A61K 36/708* | (2006.01) | |
| *A61K 36/31* | (2006.01) | |

(52) U.S. Cl.
CPC ............ *A01N 65/30* (2013.01); *A01N 43/22* (2013.01); *A01N 65/08* (2013.01); *A01N 65/20* (2013.01); *A61K 36/31* (2013.01); *A61K 36/48* (2013.01); *A61K 36/708* (2013.01); *Y02A 40/10* (2018.01)

(58) Field of Classification Search
CPC ...... A61K 36/704; A61K 36/31; A61K 36/69; A61K 36/54; A01N 43/22; A01N 65/08; A01N 45/00; A01N 63/14; A01N 65/20; A01N 65/30; A01N 35/06; A01N 63/02; Y02A 40/10; Y02A 40/143
USPC .......................... 424/758, 776, 539, 755, 739
See application file for complete search history.

(56) References Cited

U.S. PATENT DOCUMENTS

2012/0141387 A1* 6/2012 Msika .................... A61P 17/02
424/48

FOREIGN PATENT DOCUMENTS

| CN | 1515152 A | | 7/2004 |
|---|---|---|---|
| CN | 101053642 A | * | 10/2007 |
| CN | 102595885 A | | 7/2012 |
| CN | 103269583 A | | 8/2013 |
| CN | 103571657 A | * | 2/2014 |
| CN | 103918651 A | | 7/2014 |
| CN | 105192001 A | | 12/2015 |
| CN | 105211120 A | | 1/2016 |

OTHER PUBLICATIONS

State Intellectual Property Office of the P.R. China, International Search Report issued in corresponding Application No. PCT/CN2016/100604, dated Dec. 15, 2016.

* cited by examiner

*Primary Examiner* — Aaron J Kosar
(74) *Attorney, Agent, or Firm* — Stites & Harbinson, PLLC; Mandy Wilson Decker

(57) ABSTRACT

The innovations provides an antimicrobial and synergistic phytochemical composition, consisting of two active ingredients (FZ and YC). This innovation also consists of formulation processes and its applications to fungi, bacteria and/or virus-caused plant diseases such as citrus Huanglongbing, grape downy mildew, strawberry gray mold etc. This innovation combines two ingredients (FZ and YC) with different modes of action, dramatically improving plant inducible acquired resistance. Therefore, this composition dramatically enhances the control efficacy of plant diseases caused by fungi, bacteria or virus, expands the antimicrobial spectrum and promotes the plant growth.

18 Claims, No Drawings

ANTIMICROBIAL AND SYNERGISTIC PHYTOCHEMICAL COMPOSITION, ITS PREPARATION AND APPLICATIONS

TECHNICAL FIELD

This disclosure is related to an antibacterial and synergistic field for agricultural applications. In details, it is related to preparation of a composition and its applications.

TECHNICAL BACKGROUND

Anthraquinones widely exist in the roots, stems, leaves, flower and seeds of different families of plants such as Polygonaceae, Rhmnaceae, Fabaceaem, Asphodelaceae and Rubiaceae. Plants which are widely used for extracting anthraquinone are rhubarb, giant knotweed and *cassia* seeds.

Rhubarb belongs to the family of Polygonaceae. Main rhubarb includes *Rheum palmatum* L., *R. tanguticum* Maxim. ex Balf., *R. officinale* Baill.

The extract of Rhubarb is enriched with anthraquinones, which include, but not limited to, rhein, aloe-rmodin, emodin, physcion, chrysophanol, physcion-glucoside, chrysophanol-glucoside, emodin-glucoside and rhein-glucoside. For example, the extract of roots and stems of *R. palmatum* L. is composed of 2-3% anthraquinones, and about 1% of free anthraquinones. The extract of roots and stems of *R. tanguticum* Maxim. ex Balf. is composed of 5-6% anthraquinones, and about 0.8% of free anthraquinones. The extract of roots and stems of *R. officinale* Baill. is composed of 4-6% anthraquinones, and about 2.0% of free anthraquinones. In general, the roots and stems of the hybrid of *R. officinale* Baill. and *R. officinale* Baill. are used as materials for anthraquinones.

Giant knotweed, *Reynoutria sachalinensis*, belongs to the family of Polygonaceae. The extract of giant knotweed is enriched with anthraquinones and their glucosides, mainly including, but not limited to, emodin, physcion, chrysophanol, physcion glucoside, emodin glucoside, chrysophanol glucoside and resveratrol etc. Roots and stems of giant knotweed are usually used as materials for anthraquinones.

*Senna obtusifolia* belongs to the family of Fabaceae. *Cassia* seeds are generally used for herbal ingredients. The extract of the *cassia* seeds is enriched with anthraquinones, which mainly include, but not limited to, emodin, chrysophenol. physcion, obtusin, obtisifolin and their corresponding glucosides. The *cassia* seeds are usually used as the materials for anthraquinones.

The extracts of rhubarb, giant knotweed and/or *cassia* seeds are enriched with anthraquinones, possess ability to control a wide spectrum of plant diseases, almost all fungal diseases (Ascomycota, Basidiomycota, Oomycetes and Deuteromycota) and bacterial diseases such as downy mildew, gray mold, powdery mildew, rust, rice glume blight, rice blast, bacterial wilt and stem rot etc., and possess protective, curative, eradicative, penetration and systemic activity.

Except for antimicrobial activity, extracts containing anthraquinones such as giant knotweed also induce the accumulation of phytoalexins and polyphenols in plants (Daayf et al., 1995; Wurms et al. 1999; Schmitt, 2002), and therefore induce the plant defenses against plant pathogens (Vechet et al. 2009). The induced resistance of anthraquinones-containing extracts mainly exhibits on the locations where applied.

Canola Pollen Extracts

Brassinolide was the first separated and identified brassinosteroids (BRs) from Canola pollen, and possessed biological activity. Its Chinese name is Yóucài sù nèi zhǐ, CAS number is 72962-43-7, and chemical name is (3aS,5S,6R,7aR,7bS,9aS,10R,12aS,12βS)-10-[(2S,3R,4R,5S)-3,4-dihydroxy-5,6-di methyl-2-heptanyl]-5,6-dihydroxy-7a,9a-dimethylhexadecahydro-3H-benzo[c]indeno[5,4-e]oxepin-3-one.

In 1970, J. W. Mitchell separated a highly biological active substance from Canola pollen, named it as a brassinosteroid. In another 10 years, American scientists obtained 10 mg brassinosteroid from 225 kg of Canola pollen. British scientists (Mandafa et al.) obtained a highly pure brassinosteroid and its crystal structure in 1978, determining that it belongs to steroids. In 1979, Grove et al. determined its stereochemistry and named it as brassinolide (Grove et al. 1979, Nature 281: 216 217).

Brassinosteroids are the main biological principles in Canola pollen. They consist of the following compounds:

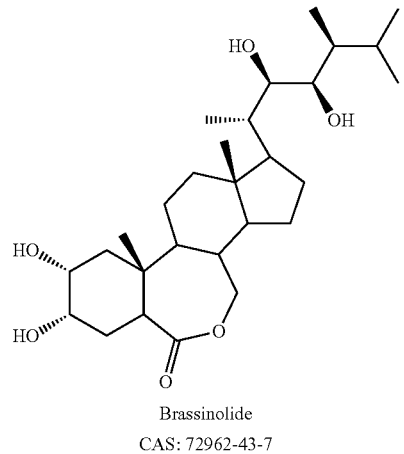

Brassinolide
CAS: 72962-43-7

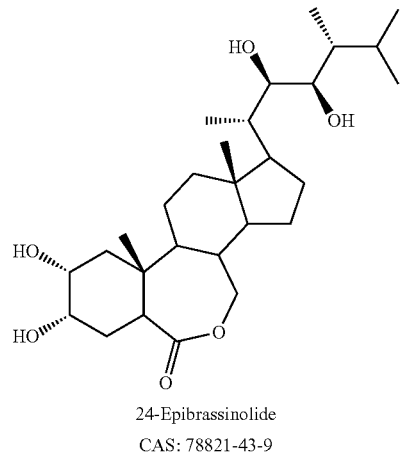

24-Epibrassinolide
CAS: 78821-43-9

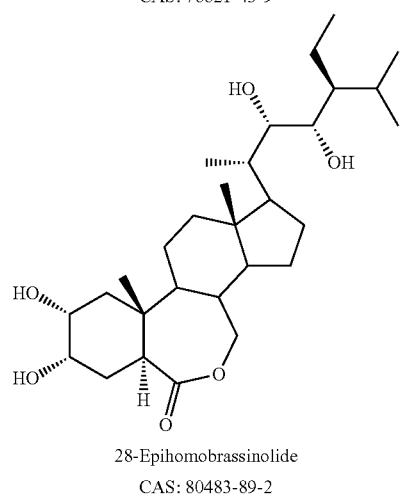

28-Epihomobrassinolide
CAS: 80483-89-2

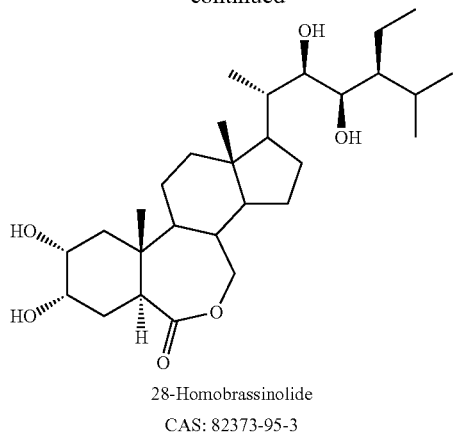

28-Homobrassinolide
CAS: 82373-95-3

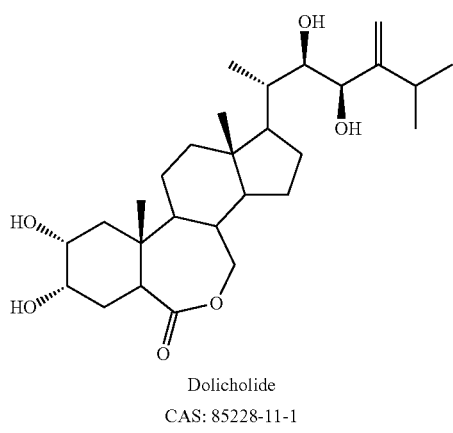

Dolicholide
CAS: 85228-11-1

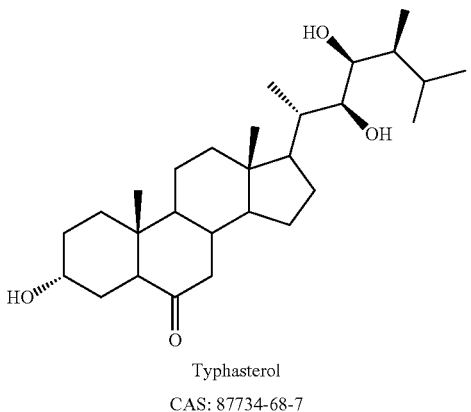

Typhasterol
CAS: 87734-68-7

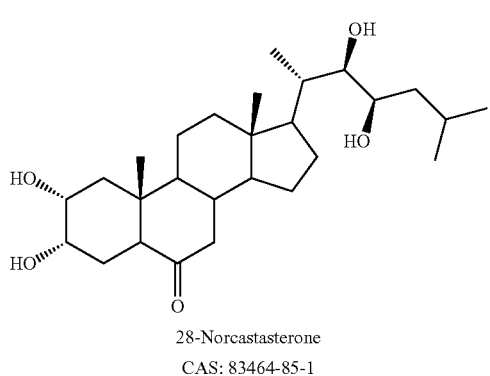

28-Norcastasterone
CAS: 83464-85-1

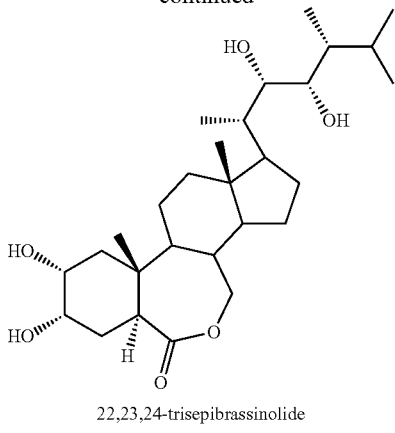

22,23,24-trisepibrassinolide
CAS: 78821-42-8

Beewax Extracts

To expand the natural resources of brassinosteroids and reduce the cost of goods, Jieguang Jiang discovered beewax could be an alternative source for brassinosteroids (CN 85102899) and Qiming He discovered that extraction of brassinosteroids could be realized through beewax hydrolysis by enzymes from *Pseudomonas fluorescens* (CN101684483).

Extracts of beewax contain brassinosteroids, which are composed of the following compounds:

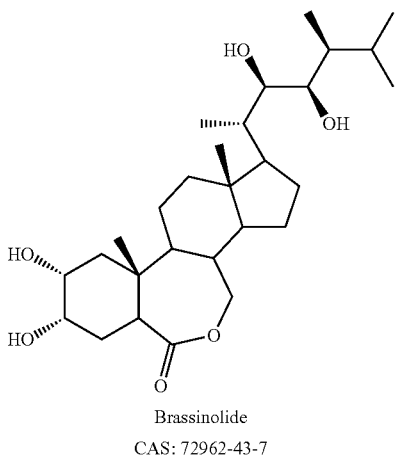

Brassinolide
CAS: 72962-43-7

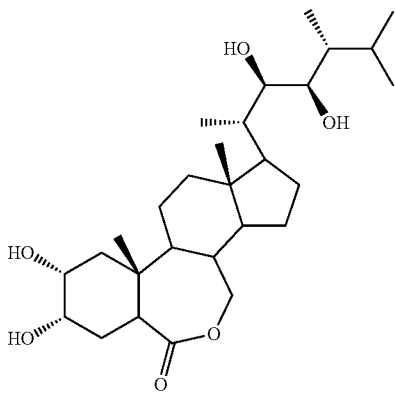

24-Epibrassinolide
CAS: 78821-43-9

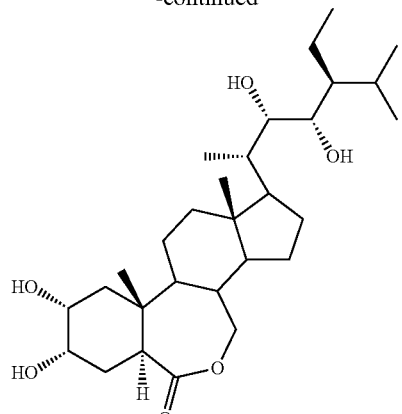

28-Epihomobrassinolide
CAS: 80483-89-2

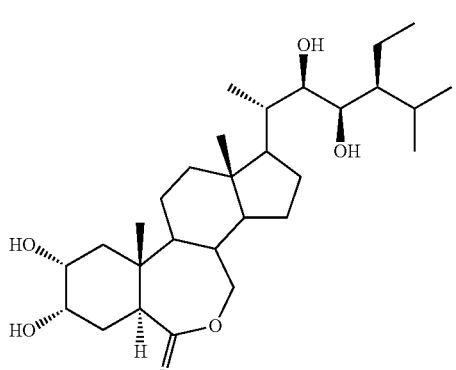

28-Homobrassinolide
CAS: 82373-95-3

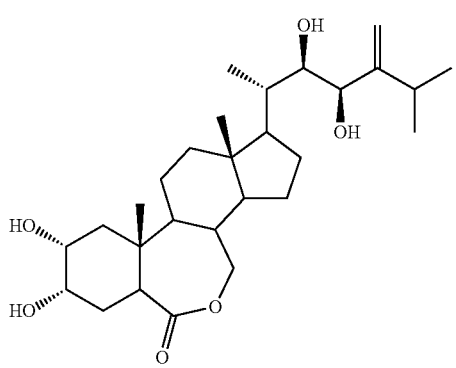

Dolicholide
CAS: 85228-11-1

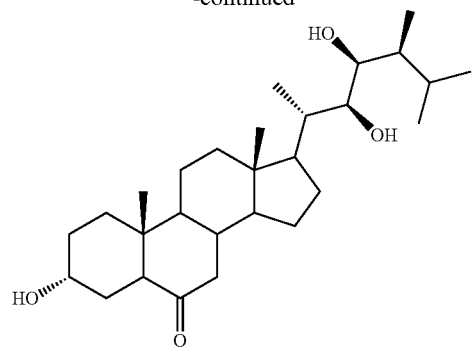

Typhasterol
CAS: 87734-68-7

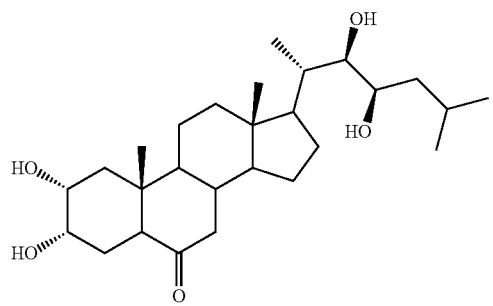

28-Norcastasterone
CAS: 83464-85-1

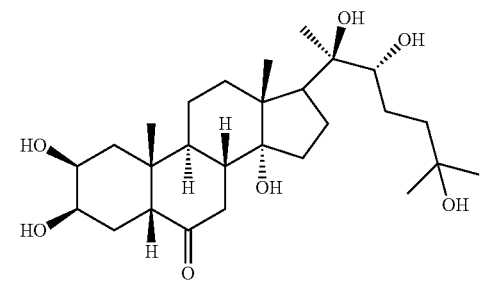

14-hydroxylated brassinosteroid
CAS: 457603-63-3

*Dolichos lablab* seeds were also discovered as an alternative source of brassinosteroids (Jun BABA et al, 1983, Agric. Biol. Chern., 47).

Synthesized Brassinosteroids

Since the identification of brassinosteroids in 1979, over 10 methods have been reported for synthesis of brassinosteroids. Due to owing the steroid backbone of all brassinosteroids, phytosteroids are usually used as staring materials for synthesis. Japanese scientist (Mori. K.) used stigmasterol as a starting material to synthesize homobrassinolide. American scientist (Thompson) adopted ergosterol as a starting material to synthesize epibrassinolide. Tkekawa et al. in Japan applied campesterol as a starting material to prepare epibrassinolide. Later. Liang Li et al. in China used phytosteriods as starting materials to synthesize three brassinosteroids such as epi-homobrassinolide (CN 891035060 and CN 981050212), which has become an industrial route. Tianchong Xia et al. started with stigmasterol and campesterol to prepare brassinolide, homobrassinolide and epibrassinolide (CN 100999542).

Synthesized brassinosteroids include the following compounds:

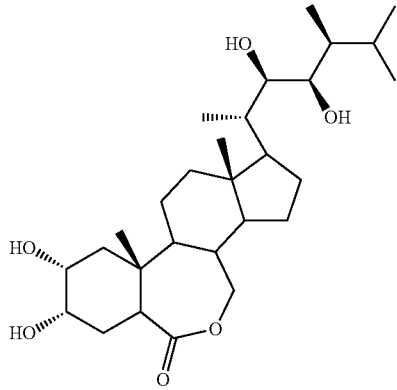

Brassinolide
CAS: 72962-43-7

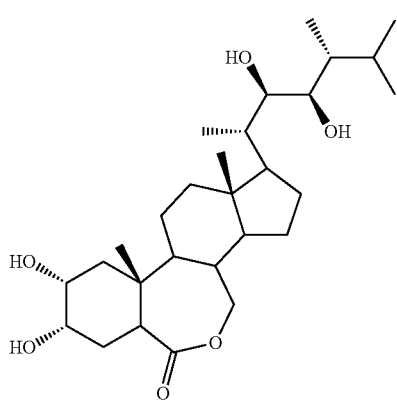

24-Epibrassinolide
CAS: 78821-43-9

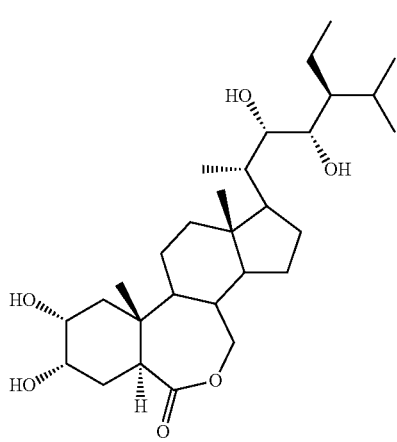

28-Epihomobrassinolide
CAS: 80483-89-2

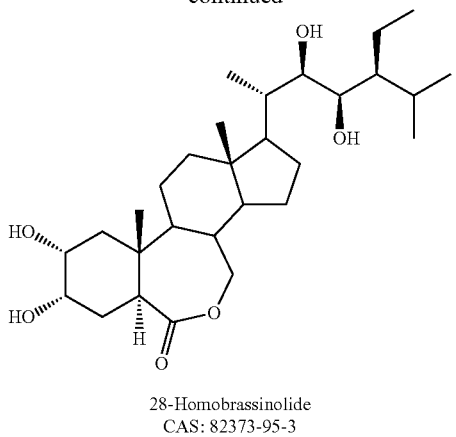

28-Homobrassinolide
CAS: 82373-95-3

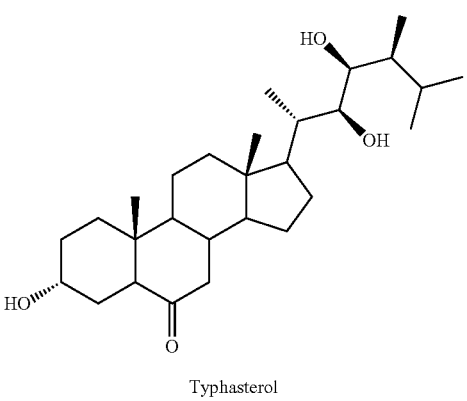

Typhasterol
CAS: 87734-68-7

Scientists have considered brassinolide as the sixth auxin after plant growth auxin, gibberellin, cytokinin, abscisic acid and ethylene. It is widely considered as a plant auxin with the highest biological activity, broad spectrum and harmlessness. Plant physiologists generally consider that it can fully stimulate the plant's inner potential, promote the plant growth and improve the plant yield, enhance crop cold, disease and salt resistance, and improve crop defense and reduce the side-effects of herbicides on crops.

Over the last few decades, scientists have fully studied the mode of action and biological efficacy of brassinolide, mainly focused on the cell elongation and plant growth. Brassinolide possesses an obvious effects on cell elongation, its effective concentration is a few orders lower than plant auxin. Brassinolide promotes proton pump to transfer hydrogen ions out of cell membrane, leading to acidification of intercellular environment, so as to promote the growth of cell wall relaxation. At the same time, brassinolide can also inhibit the activity of growth hormone oxidases, enhance the content of plant inner growth hormone. Therefore, there will be a synergistic effect when combined with plant growth hormone and brassinolide. In addition, brassinolide can also regulate the synthesis and metabolism of some plant growth-related proteins, leading to regulating plant growth. Brassinolide mainly locates at the site of vigorous plant growth. Brassinolide also regulates the nutrient distribution in plants, enhances the dry weight under the treated site and, in contrast, decreases the dry weight above the treated site, but maintain the consistency of plant total dry weight.

Moreover, brassinolide can also affect the metabolism of nucleus and slow the senescence of plant cells in vitro.

Except for functioning as plant growth regulator and plant growth hormone, natural and synthesized brassinosteroids have been found to induced systemic resistance (ISR) of plants against bacterial and fungal pathogens (Nakashita et al., 2003, Plant Journal 33:887 898). Antimicrobial activity locates at the whole plants.

Although FZ, YC, and the combinations of FZ or YC with other active ingredients have been known in pesticide field, antimicrobial activity and plant growth regulation of the composition of FZ and YC has not been reported, especially no attention has been paid on their synergistic effects on induced systemic resistance against bacterial, fungal and viral pathogens and promoting plant growth.

Innovation

The aim of this innovation is to provide a synergistic composition with functions of antimicrobial activity and promoting plant growth, preparation and its applications The active ingredients of disclosed composition in this innovation are FZ and YC.

The preparation of the composition was also disclosed in this innovation. The formulation types include, but not limited to, following: emulsifiable concentrate (EC), aqueous emulsion (EW), microemulison (ME), suspension concentrate (SC), oil dispersion (OD), capsule suspension (CS), wettable powder (WP), water dispersible granule (WDG), soluble powder (SP), soluble granule (SG), suspension emulsion (SE), flowable concentrate for seed treatment (FS), aqueous solution (AS) and ready to use formulation.

This innovation also provides the applications of the composition on inhibiting plant bacterial, fungal and viral pathogens, promoting plant growth, enhancing the plant resistance under stresses and improving the crop yields.

As mentioned above, FZ is extracted from the roots, stems, flower and seeds of Polygonaceae, Rhmnaceae, Fabaceae, Asphodelaceae, Rubiaceae. Anthraquinones and their corresponding glucosides are the main biological principles. Common plant materials for anthraquinones are rhubarb, giant knotweed and *cassia* seeds.

Anthraquinones from rhubarb include, but not limited to, rhein, aloe-emodin, emodin, physcion, chrysophanol, physcion-glucoside, chrysophanol-glucoside, emodin-glucoside and rhein-glucoside etc.

Anthraquinones from giant knotweed include, but not limited to, emodin, physcion, chrysophenol, emodin-glucoside, physcion-glucoside, chrysophanol-glucoside and resveratrol etc.

Anthraquinones from *cassia* seeds include, but not limited to, emodin, chrysophanol, physcion, obtusin, obtusifolin and their corresponding glucosides etc.

As mentioned above, YC is extracted from canola pollen (e.g., pollen of *Brassica napus* L.) and beewax (direct extraction of beewax or extraction after enzymatic hydrolysis of beewax), and YC can be synthesized brassinosteroids. The extracts of both canola pollen and beewax include the brassinosteroids.

The extract of canola pollen includes the brassinosteroids, which consists of one or multiple following compounds:

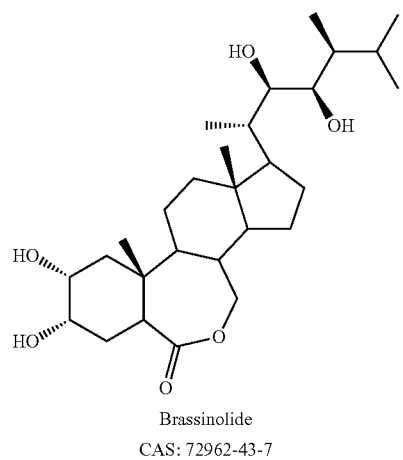

Brassinolide
CAS: 72962-43-7

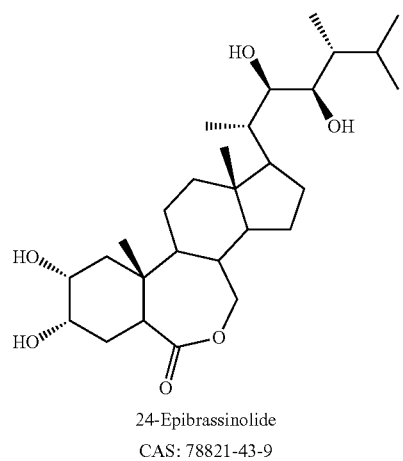

24-Epibrassinolide
CAS: 78821-43-9

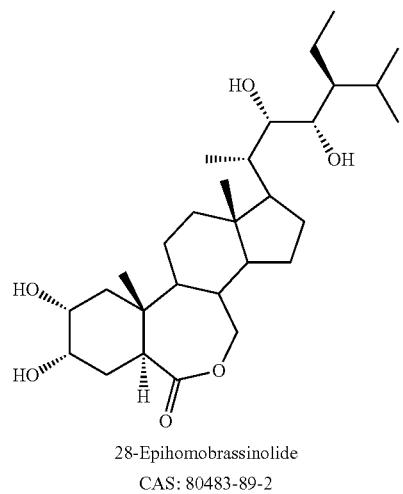

28-Epihomobrassinolide
CAS: 80483-89-2

-continued
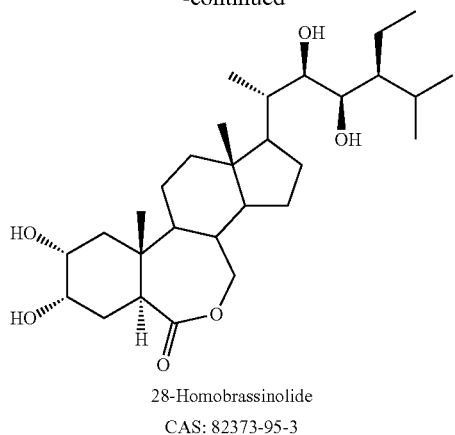
28-Homobrassinolide
CAS: 82373-95-3
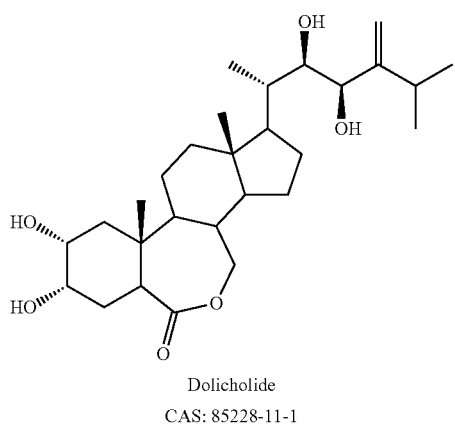
Dolicholide
CAS: 85228-11-1
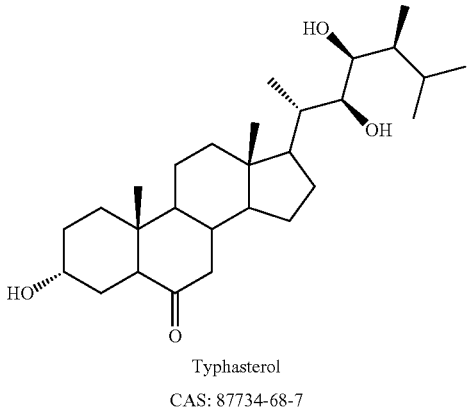
Typhasterol
CAS: 87734-68-7
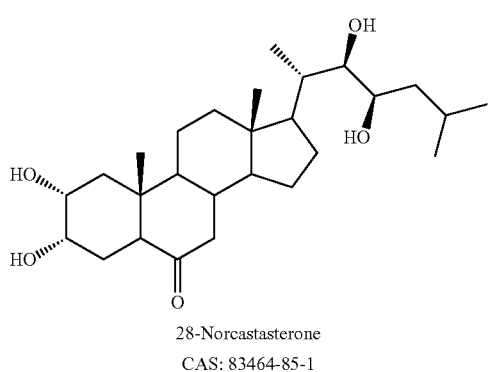
28-Norcastasterone
CAS: 83464-85-1
-continued
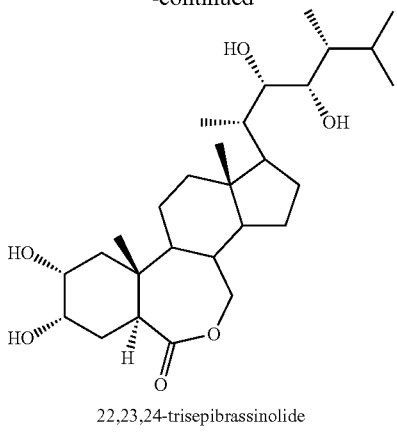
22,23,24-trisepibrassinolide
CAS: 78821-42-8
the extract of beewax includes the brassinosteroids, which consists of one or multiple following compounds:
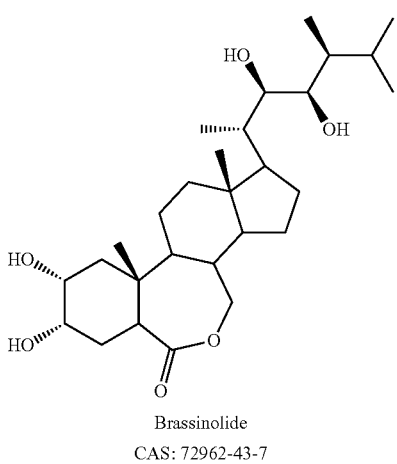
Brassinolide
CAS: 72962-43-7
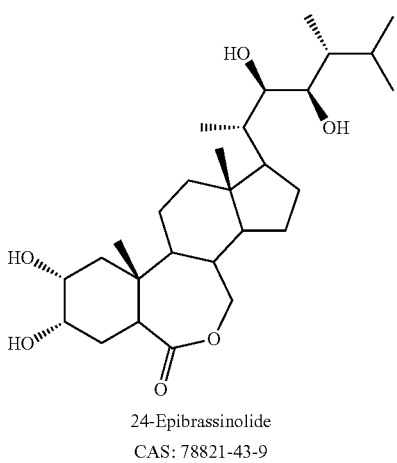
24-Epibrassinolide
CAS: 78821-43-9

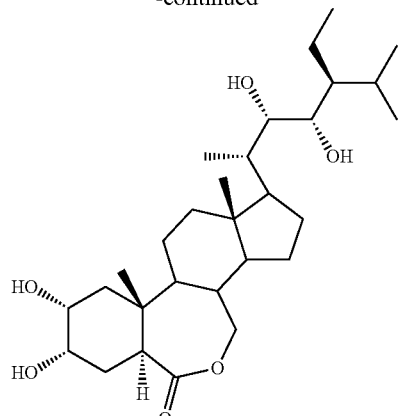
28-Epihomobrassinolide
CAS: 80483-89-2
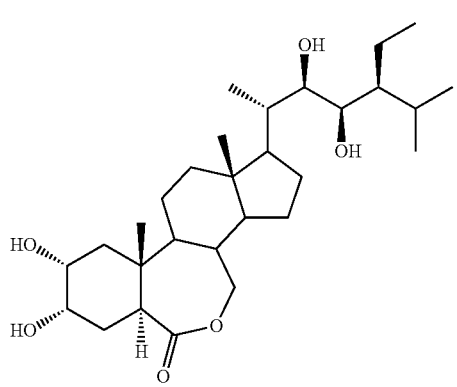
28-Homobrassinolide
CAS: 82373-95-3
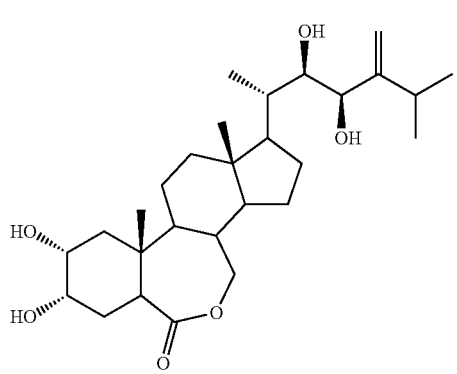
Dolicholide
CAS: 85228-11-1
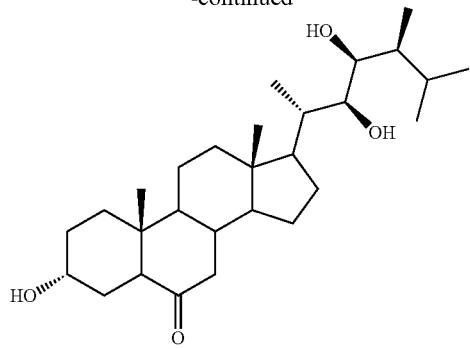
Typhasterol
CAS: 87734-68-7
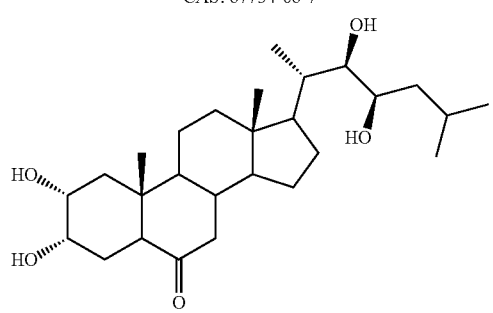
28-Norcastasterone
CAS: 83464-85-1
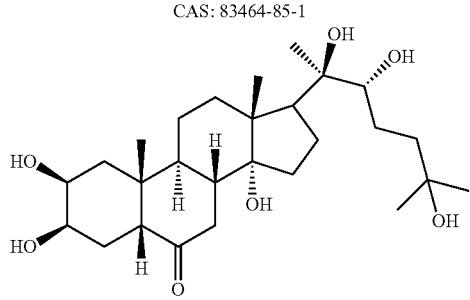
14-hydroxylated brassinosteroid
CAS: 457603-63-3
The synthesized brassinosteroids include one or multiple following compounds:
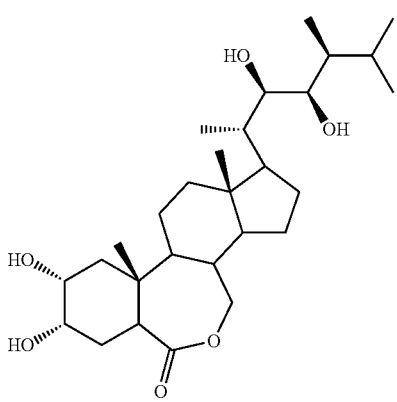
Brassinolide
CAS: 72962-43-7

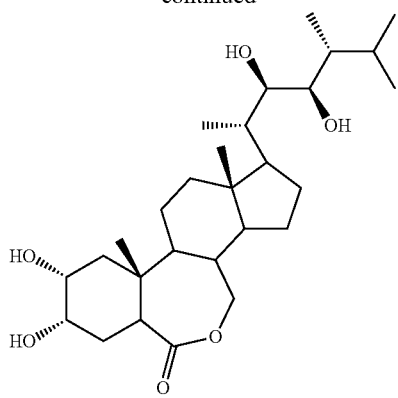

24-Epibrassinolide
CAS: 78821-43-9

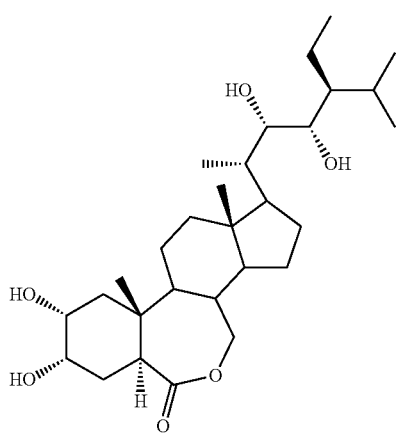

28-Epihomobrassinolide
CAS: 80483-89-2

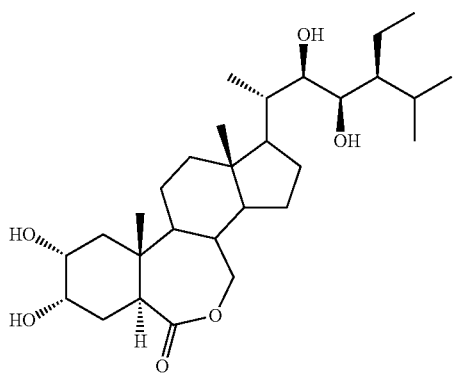

28-Homobrassinolide
CAS: 82373-95-3

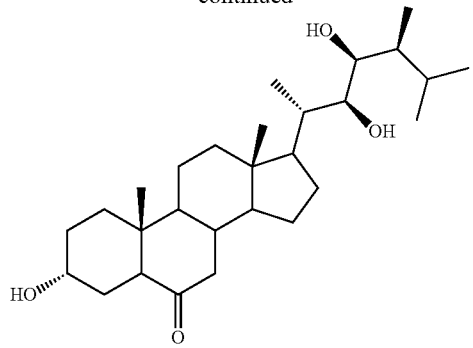

Typhasterol
CAS: 87734-68-7

In the preferred embodiment of the present invention, FZ is preferably giant knotweed extract and *cassia* seed extract, and further preferably giant knotweed extract. YC is preferably beewax extract and synthesized brassinosteroids, and further preferably beewax extract.

Accumulated data from the inventor demonstrated that it was very obvious that the composition of FZ and YC improved the crop yield, enhanced plant resistance and boosted plant resistance against plant pathogens.

In the present invention, weight ratio of FZ and YC can be changed within a wide range, in particular, weight ratio of FZ and YC can be from 0.0001:1 to 1000000:1, preferably from 0.001:1 to 100000:1, more preferably from 0.01: 10 to 10,000:1.

In the present invention, the concentration ratio of the FZ and YC may be from 1000 ppm:0.001 ppm to 1 ppm:500 ppm, more preferably from 500 ppm:0.01 ppm to 5 ppm:200 ppm.

In the present invention, the active ingredients in the composition can be varied over a wide range, in particular, the active ingredient FZ in the composition can be in an amount of 0.001% (w/w) to 99% (w/w), preferably from 0.01% (w/w) to 60% (w/w); the active ingredient YC in the composition can be in an amount of 0.000001% (w/w) to 60% (w/w), preferably from 0.00001% (w/w) to 40%.

In the present invention, in addition to active ingredients, the composition typically further comprises at least two carriers, at least one and preferably as additives, such as surfactants.

such surfactants may be known in the art that various surfactants, preferably present in present invention one or multiple of the emulsifiers, dispersants or wetting agents:

Other carriers that, in addition to the above-described surfactants, are known in the art, can be various carriers, specifically, for example: one or more of carbon black, kaolin, diatomaceous earth, clay, talc, bentonite, pumice, titanium oxide, dextrin, mixture of cellulose powder, calcium carbonate, a soluble starch, urea, ammonium fertilizer, mixture of urea and ammonium fertilizer, glucose, maltose, table sugar, anhydrous potassium carbonate, anhydrous sodium carbonate, anhydrous potassium bicarbonate, anhydrous sodium bicarbonate, mixture of anhydrous potassium carbonate and anhydrous potassium bicarbonate, and mixture of anhydrous sodium carbonate and anhydrous sodium bicarbonate;

Such emulsifiers that are known in the art may be a variety of emulsifiers, in particular, the emulsifier may be one or multiple of following: calcium dodecanyl sulfate, lecithin, sorbitan fatty acid ester, polyoxyethylene sorbitan fatty acid ester, polyoxyethylene fatty acid ester, polyoxyethylene fatty acid diester, polyoxyethylene fatty alcohol ether, polyoxyethylene fatty amine, ethoxylated castor oil, polyoxyethylene hydrogenated castor oil, polyethylene glycol fatty acid esters, alkylphenol polyoxyethylene ether, polyoxyethylene alkylphenyl ether, polyoxyethylene dialkylphenyl ether, polyoxyethylene alkylphenyl ether/formaldehyde condensate, polyoxyethylene/polyoxypropylene block polymer ether, polyoxyethylene diphenyl ether, polyoxyethylene benzyl phenyl ether, polyoxyethylene styryl phenyl ether, polyoxyethylene ether silicone, ester type silicones, polyoxyethylene fatty alcohol ethers, fatty alcohol (polyoxyethylene) ether, sodium sulfosuccinate, and alkylphenol polyoxypropylene polyoxyethylene ether.

The dispersant mentioned above may be the art of the various known dispersants, in particular, the dispersant is one or multiple of the following: lignin sulfonate, polyacrylic acid sodium, naphthalene sulfonate, alkylnaphthalene sulfonate, methylene-bis-naphthalene sulfonate, alkylamide taurates, poly-carboxylic acid salt, alkylnaphthalene sodium sulfate, alkylnaphthalene formaldehyde polymer.

The wetting agent mentioned above may be the art of the various known wetting agents, in particular, the wetting agent is one or multiple of the following: sodium lauryl sulfate, secondary alkyl sodium sulfate, sodium dodecyl benzenesulfonate, fatty alcohol polyglycol ether sulfates, and mixture of alkylnaphthalene sulfate with an anionic wetting agent;

The compositions of the invention may also contain a variety of commonly used in the art formulation additives, in particular, the formulation additives can be one or multiple of the followings: solvents, co-solvents, thickeners, antifreeze, capsule material, protective agents, defoamers, disintegrating agents and a binder.

Solvents described above may be well known in the art a variety of solvents, specifically, the solvent may be one or multiple of the following: an organic solvent, vegetable oil, mineral oil, solvent oil and water.

Wherein said organic solvent comprises N-methyl pyrrolidone, tetrahydrofuran, dimethylsulfoxide, N, N-dimethyl decanamide, N, N-dimethylformamide, xylene, tetrahydrofurfuryl alcohol, tributyl phosphate, 1, 4-dioxane or cyclohexanone: the vegetable oils includes one or multiple of the following: epoxidized soybean oil, soybean oil, peanut oil, rapeseed oil, castor oil, corn oil and pine oil.

The mineral oils include one or multiple of the following: liquid paraffin, oil, kerosene and lubricants.

The solvent oils include Solvesso 100, Solvesso 150 or Solvesso 200.

Meanwhile, these solvents can be used as co-solvents.

Antifreeze mentioned above is well known in the art a variety of antifreeze, the present invention is preferably one or multiple of the following: ethylene glycol, propylene glycol, glycerin and urea.

The thickener mentioned above may be the various known art thickeners, in particular, the thickener may be one or multiple of the following: xanthan gum, polyvinyl alcohol, polypropylene glycol, polyethylene glycol, carbon black, diatomaceous earth, kaolin, clay, sodium alginate, aluminum silicate, sodium silicate, carboxymethyl cellulose, hydroxypropyl cellulose and sodium bentonite.

Capsule materials mentioned above may be known in the art a variety of capsule materials, preferably in present invention is one or multiple of the following: polyurethane, polyurea or urea-formaldehyde resin.

Protective agents mentioned above may be known in the art a variety of protective agents, preferably in present invention is polyethylene alcohol and/or polyglycol.

Antifoaming agent said here may be known in the art the various defoamers, the present invention is preferably one or multiple of the following: organosiloxane, tributyl phosphate and silicone.

The present invention further provides formulation types of the composition mentioned above. Such formulation types include emulsifiable concentrate (EC), aqueous emulsion (EW), microemulison (ME), suspension concentrate (SC), oil dispersion (OD), capsule suspension (CS), wettable powder (WP), water dispersible granule (WDG). Soluble powder (SP), soluble granule (SG), suspension emulsion (SE), flowable concentrate for seed treatment (FS), aqueous solution (AS) and ready-to-use formulation.

Formulations of the present invention may be well known in the art in various forms, in particular, it can be emulsifiable concentrate (EC), aqueous emulsions, aqueous suspensions, oil dispersion, capsule suspensions, wettable powders, water dispersible granules agents, soluble powders, soluble granules or micro-emulsions, suspoemulsions (SE), suspension seed formulation (FS), aqueous solution (AS) and ready-to-use formulation (Ready-to-use formulation). The formulation mentioned above can be prepared by conventional methods in the art. For example, The total content of the active ingredient in the emulsifiable concentrate formulation (EC) is from 0.01% to 95% by weight, co-solvent content from 0% to 20% by weight, the emulsifier content is from 1% to 30% by weight, solvent made up to 100%.

The preparation methods of EC formulation mentioned above may comprise of, for example, blending each of the active ingredients, solvents, co-solvent or solubilizers and emulsifiers to make a homogeneous oil phase, therefore, obtain an emulsifiable concentrate formulation (EC).

Aqueous emulsion or microemulsion described in present invention comprises by weight: active ingredient from 0.01% to 95%, Emulsifier from 1% to 30%, co-solvent from 0% to 30% 0%, solvent from 1% to 30%, antifreeze from 0% to 10%, thickener from 1% to 10%, made up to 100% with water.

The method of preparing the above-described aqueous emulsions or microemulsions for example, may comprise of blending the active ingredient, an emulsifier, a co-solvent and solvent to form a uniform oil phase: mixing water, thickeners, antifreeze, etc. to obtain a homogeneous the aqueous phase. Under high speed stirring, the aqueous phase is added to the oil phase or oil phase is added to the aqueous phase, forming well dispersed aqueous emulsion or microemulsion. Wherein the microemulsion is transparent appearance, water emulsion is suspension.

Aqueous suspension described in present invention comprises by weight: active ingredient from 0.01% to 95%, surfactants from 1% to 30%, antifreeze from 0% to 10%, thickener from 1% to 5%, made up to 100% with water.

Oil dispersion described in present invention comprises by weight: active ingredient from 0.01% to 95%, surfactants from 1% to 30%, thickener from 0.1% to 0.5%, made up to 100% with oil.

The methods of preparation aqueous/oil suspension mentioned above are as follows: use either water or oil as a media, grind the active ingredients, surfactants, thickeners to make fine particles, forming the aqueous or oil suspension.

The soluble granules, soluble powders, water dispersible granules, or wettable powder described in present invention comprises by weight: active ingredients from 0.01% to 95%, surfactants from 1% to 30%, make up to 100% with various carriers.

Among them, the preparation of water-dispersible granules, soluble granules are as follows: mix each active ingredient and other carriers and mill them, dry the mixture by spraying drying or boiling drying to obtain final products: or knead the mixed crushed powder with water, granulate with a granulator, final granules are obtained by drying and sieving through 5-60 mesh.

The preparation method of soluble powders and wettable powder described in present innovation is as follows: fully mix each of the active ingredients, various additives and fillers such as other carriers well and mill the mixture with a superfine grinding mill.

The capsule suspension described in present invention comprises by weight: active ingredients from 0.01% to 95%, solvents from 1% to 30%, protective agents from 0.1% to 5%, defoamers from 0.05% to 1.0%, capsule material from 1% to 30%, dispenser from 1% to 30%, antifreeze from 1% to 10%, thickener from 0.1% to 5%, make up to 100% with water.

The preparation method of capsule suspension described in present innovation is as follows: mix the solvent with capsule material; add the active ingredients to form a mixture; add such a mixture into another mixture consisting of protective agent, antifreeze, defoamer and water to emulsify, stir the mixture until polymerization is completed, then thickener, dispenser and wetting agents are added to form a stable capsule suspension.

The present innovation also provides the applications of the composition against the fungi, bacteria and/or virus-caused plant diseases.

The compositions of the present invention may be provided in a form of finished formulations, i.e. the compositions of each substance have been mixed: can also be provided in a single formulation form, mixed in a tub or tank themselves prior to use, the concentrates are usually mixed with water to give the desired concentration of the active ingredients.

The compositions of the present invention are useful in a variety of crops, such as cucumbers, pumpkin, zucchini, tomatoes, onions, green onions, beets, peppers and other vegetables: wheat, cereals, rice and other row crops: mung bean, tobacco, flax and other economic crops: strawberries, grapes, citrus and other fruit crops or trees: peony, *chrysanthemum*, roses and other flowers and other ornamental and garden plants.

There is an obvious synergism when the composition of the present invention is compared with the corresponding individual active component. Good efficacy is against plant diseases such as powdery mildew, downy mildew, late blight, frost blight, *Pythium*, damping-off disease, black stem disease, canker, early blight, scab, rust, *septoria nodorum* blotch, net blotch, leaf blight, blast charcoal, gray mold and other plant diseases, especially extremely effective against cucumber downy mildew, powdery mildew, citrus Huanglongbing, rice blast and sheath blight.

Application method of the composition of the present invention is simple, prior to or after disease appearance, applying it to plants or their growth environments with conventional methods such as soil mixing, spraying, dipping, drenching etc., its application rate may be adjusted according to climate condition and/or crops. Under normal circumstances, 1-1000 g/mu is applied. The application concentration is from 0.001 to 1000 mg/L, diluted, preferably, with water.

In the present invention, the experiment proved very surprising synergistic effects by mixing active principles of FZ and YC with different induced resistance mechanisms, the mixture obviously enhanced control effects of fungi, bacteria and/or virus-caused plant diseases, expanded the antimicrobial spectrum and obviously promoted plant growth and improved the crop yields.

In summary, the compositions of the present invention possess the following advantages:

The compositions of FZ and YC within a certain concentration range exhibit excellent synergistic effect; When compared with either an individual active principle, the compositions significantly improved antimicrobial effect, thereby reducing the amount of active principles, aligning with reducing farmers' costs and the impact on the environment.

Expansion of antimicrobial spectrum leads to control of multiple plant diseases with one product, providing a convenient and effective means of disease prevention and protection.

The composition is a combination of an antimicrobial agent and a plant growth regulator, so that different interaction characteristics between the two agents have a very strong complementary advantages, can effectively delay the occurrence and development of resistance to an individual agent.

DETAILED EXPERIMENTS

By the following specific embodiments of the present invention is further illustrated, but the present invention is not limited only to the following examples. The content of the following examples is expressed by percent of weight.

Some substances in the following examples were purchased from different companies: polyurea from Dongsheng Futian Jufu Company, organosiloxane from Mianyang Huili Huanyang Co. Ltd., sodium ligninsulfonate and calcium lignosulfonate from Henan Anyang Chemical Industry, polyoxyethylene styryl phenyl ether from Nanjing Taihua chemical industry, polypropylene alcohol from Beijing Baishun Chemical Tech Co. Ltd., sec-octyl phenol polyoxyethylene ether, fatty alcohol polyoxyethylene ether and polyoxyethylene fatty acid ester from Tianjin Hongmei Chemical Industry, kaolin from Anhui Tongling Guotai Non-metallic Materials Co., paraffin oil from Beijing Huaye Hongyu Chemical Co., Ltd, fatty alcohol polyglycol ether sulfate from Shanghai Youwen Chemical Co., urea (available from Annhui JinAo Chemical Co., Ltd., Alkyl phenol polyoxyethylene ether from Beijing Huayou Chemical Co., methylene bis-naphthalene sulfonate sodium, alkyl naphthalene-sulfonic acid formaldehyde condensate and alkyl naphthalene sulfonic acid salt from Beijing Chemical Reagent Factory.

Preparation methods of suspension spores used for spraying inoculation in the following examples is as follows: spray distilled water onto the diseased leaves, collect the spore solution and adjust it into a spore concentration of $10^5$/mL.

Preparation of rhubarb extract: crush Rhubarb roots after drying, ferment, extract with ethanol-water mixture, concentrate, hydrolyze, neutralize, extract with ethyl acetate, concentrate to obtain rhubarb extracts.

Preparation of giant knotweed extract: crush giant knotweed roots after drying, ferment, extract with ethanol-water mixture, concentrate, hydrolyze, neutralize, extract with ethyl acetate, concentrate to obtain giant knotweed extracts.

Preparation of *cassia* seed extract: crush *cassia* seeds after drying, ferment, extract with ethanol-water mixture, concentrate, hydrolyze, neutralize, extract with ethyl acetate, concentrate to obtain *cassia* seed extracts.

Preparation of canola pollen powder extract: crush the canola pollens, extract with ethanol-water, concentrate the extraction solution and then extract with ethyl acetate, concentrate the ethyl acetate layer to obtain canola pollen extract.

Preparation of beeswax extract: emulsify the beewax with water and emulsifier to form a dispersion solution, add 2000-3000U/L degrading enzyme solution (e.g., enzyme solution from *Pseudomonas fluorescens* fermentation), adjust the pH and temperature, fully hydrolyze, extract the hydrolyzed solution with ethanol and n-hexane, concentrate to obtain the beewax extract.

Preparation of synthetic brassinosteroids: usually from phytosterol alcohols such as stigmasterol. Synthetic brassinosteroids can be obtained after a series of sequential reactions: sulfonylation, cyclization, oxidation, ring-opening, the catalytic oxidation and esterification.

After purification, over 80% technical grade of active ingredients such as brassinolide, 80% typhasterol and 80% 14-hydroxylated brassinosteroid can be obtained from Canola pollen extract, beeswax extract, or synthetic brassinosteroids.

Example 1: Capsule Suspension: 0.5% of Active Ingredients

Formula composition: rhubarb extract (4.995 g), 80% brassinolide technical grade (0.005 g), 150 solvent oil (solvent, 21 g), polyurea (capsule material, 3 g), polyvinyl alcohol (protecting agent, 1.0 g), organosiloxane (defoamers, 0.05 g), xanthan gum (thickener, 0.15 g), sodium lignin sulfonate (dispersing agent, 3 g), add water made up to 1 kg.

Preparation method: The mixture of FZ, YC, No. 150 solvent oil and polyurea was added into another mixture consisting of polyvinyl alcohol, organosiloxane and water to emulsify, stirred until the polymerization reaction was completed; added xanthan gum and sodium lignin sulfonate to form a stable capsule suspension. The median capsule diameter was 5-8 microns. This product was coded as A1.

Example 2: Aqueous Emulsion: 5% of Active Ingredients

Formula composition: giant knotweed extract (49.875 g), 80% typhasterol technical grade (0.125 g), No 150 solvent oil (50 g), polyoxyethylene styrene phenyl ether (emulsifier, 50 g), polypropylene alcohol (thickener, 80 g), diatomaceous earth (carrier, 30 g) add water made up to 1 kg.

Preparation method: combined the FZ, YC, NO 150 solvent oil and polyoxyethylene styrene phenyl ether to make a homogenous oil phase; added diatomaceous earth into water to form a homogeneous aqueous phase; under high speed stirring, added the aqueous phase into oil phase to form 5% aqueous suspension with good dispersing property. This product was coded as A2.

Example 3: Microemulsion: 15% of Active Ingredients

Formula composition: giant knotweed extract (75 g), canola pollen extract (75 g), N-methylpyrrolidone (co-solvent, 50 g), sec-octyl phenol ethoxylates (emulsifier, 100 g), ethoxylated castor oil (emulsifier, 200 g), ethylene glycol (antifreeze, 50 g), water made up to 1 kg.

Preparation method: Made homogeneous oil phase by adding FZ, YC, N-methyl pyrrolidone, sec-octylphenol polyoxyethylene ether and ethoxylated castor oil: added glycol into water to form a uniform aqueous phase; under high speed stirring, the aqueous phase was added to the oil phase to form a microemulsion containing 15% of active ingredients. This product was coded as A3.

Example 4: Aqueous Suspension: 4.5% of Active Ingredients

Formula composition: *Cassia* seed extract (44.8 g), beeswax extract (2 g), ethoxylated castor oil (emulsifier, 10 g), fatty alcohol polyethoxyethylene ether (emulsifier, 30 g), diatomaceous earth (thickener, 30 g), propylene glycol (antifreeze, 60 g), water made up to 1 kg.

Preparation method: Water was used as a medium, the FZ, YC, ethoxylated castor oil, fatty alcohol polyoxyethylene ether, diatomaceous earth and glycol were added into sand mill to grind fine particle, forming aqueous suspensions containing 4.5% active ingredients. This product was coded as A4.

Example 5: Oil Dispersion, 50% of Active Ingredients

Formula composition: giant knotweed extract (499.8 g), 80% 14-hydroxylated brassinosteroid technical grade (0.2 g), polyoxyethylene fatty alcohol ether (emulsifier, 100 g), polyoxyethylene fatty acid ester (emulsifier, 50 g), kaolin (thickener, 30 g), paraffin oil made up to 1 kg.

Preparation method: Paraffin oil was used as the medium. The FZ, YC, polyoxyethylene fatty alcohol ether, polyoxyethylene fatty acid ester and kaolin were added into sand mill to grind fine particles, forming an oil suspension containing 50% active ingredient. This product was coded as A5.

Example 6: Soluble Granules, 20% of Active Ingredients

Formula composition: Rhubarb extract (199.5 g), beeswax extract (0.5 g) calcium lignosulfonate (dispersants, 50 g), fatty alcohol polyglycol ether sulfate (wetting agent, 50 g), urea (carrier) to make up to 1 kg.

Preparation method: The FZ, YC, calcium lignosulfonate, fatty alcohol polyglycol ether sulfate and urea were mixed and pulverized, added water, granulated it with a granulator with diameter of 1.0 mm sieve, dried, and sieved through 30 mesh sieve to prepare a water-dispersible granules containing 20% of active ingredients. This product was coded as A6.

Example 7: Emulsifier Concentrate, 70% of Active Ingredients

Formula composition: *Cassia* extract (600 g), canola pollen extract (100 g), alkylphenol polyoxyethylene ether (emulsifier, 50 g), fatty alcohol polyoxyethylene ether (emulsifier, 50 g), No 150 solvent oil made up to 1 kg, mixed all and formed a homogeneous oil phase, i.e., emulsifier concentrate 70% of the active ingredient. This product was coded as A7.

Example 8: Wettable Powder, 80% of Active Ingredients

Formula composition: Rhubarb extract (784 g), beeswax extract (16 g), sodium lignosulphonate (dispersant, 30 g), methylene-bis-naphthalene sulfonate (dispersing agent NNO, 20 g), soluble starch (carrier, 50 g), kaolin (carrier) made up to 1 kg.

Preparation method: The components described above were thoroughly mixed, ground with a superfine grinding mill to obtain a wettable powder containing 80% of active ingredients. This product was coded as A8.

Example 9: Water Dispersible Granules, 90% of Active Ingredients

Formula composition: giant knotweed extract (896 g), beeswax extract (4 g), calcium lignosulfonate (dispersants, 50 g), fatty alcohol polyglycol ether sulfate (wetting agent, 50 g), urea (vector) made up to 1 kg.

Preparation method: The FZ, YC, calcium lignosulfonate, fatty alcohol polyglycol ether sulfate and urea were mixed and pulverized, added water, granulated with a granulator equipped with a diameter of 1.0 mm sieve, dried and then sieved through a 30 mesh sieve, forming water-dispersible granules containing 90% of active ingredients. Tis product was coded as A9

Example 10: Soluble Powder, 95% of Active Ingredients

Formula composition: Giant knotweed extract (949.05 g), 80% brassinolide technical grade (0.95 g), alkylnaphthalene sulfonic acid formaldehyde condensate (30 g), alkylnaphthalene sulfonate (wetting agent, 20 g), Preparation method: The components described above were thoroughly mixed, ground with a superfine grinding mill to obtain soluble powder containing 95% of the active ingredient. This product was codes as A10.

Example 11: Aqueous Solution, 30% of Active Ingredients

Formula composition: Giant knotweed extract (25 g), beeswax extract (275 g), ethanol (co-solvent, 50 g), ethylene glycol (antifreeze, 50 g), water made up to 1 kg.

Preparation method: Mixed the giant knotweed extract, beewax extract and ethanol to form a homogeneous oil phase; added ethylene glycol into water to form a homogeneous aqueous phase; under high speed stirring, the oil phase was added to the aqueous phase to form a good aqueous solution containing 30% of active ingredients. This product was coded as A11.

Control Formulation 1: Oil Dispersion, 3% Rhubarb Extract

Formula composition: Rhubarb extract (30 g), polyoxyethylene fatty alcohol ethers (emulsifier, 30 g), polyoxyethylene fatty acid ester (emulsifier, 10 g), kaolin (thickener, 10 g), paraffin oil made up to 1 kg.

Preparation method: Paraffin oil was used as the medium. The rhubarb extract, polyoxyethylene fatty alcohol ether, polyoxyethylene fatty acid ester and kaolin were added in sand grinding mill to obtain an oil dispersion containing 3% active ingredient. This product was coded as C1.

Control Formulation 2: Microemulsion, 5% Giant Knotweed Extract

Formula composition: giant knotweed extract (50 g), N-methylpyrrolidone (co-solvent, 20 g), sec-octylphenol polyoxylethylene ether (emulsifier, 40 g), ethoxylated castor oil (emulsifier, 80 g), ethylene glycol (antifreeze, 30 g), water made up to 1 kg.

Preparation method: Made homogeneous oil phase by adding giant knotweed extract, N-methyl pyrrolidone, sec-octylphenol polyoxyethylene ether and ethoxylated castor oil: added glycol into water to form a uniform aqueous phase; under high speed stirring, the aqueous phase was added to the oil phase to form a microemulsion containing 5% of active ingredient. This product was coded as C2.

Control Formulation 3: Soluble Powder, 10% *Cassia* Seed Extract

Formula composition: *Cassia* extract (100 g), alkyl naphthalene sulfonic acid formaldehyde condensate (dispersant, 10 g), alkylnaphthalene sulfonate (wetting agent, 10 g), soluble starch made up to 1 kg Preparation method: The components described above were thoroughly mixed, ground with a superfine grinding mill to obtain soluble powder containing 10% of the active ingredients. This product was coded as C3.

Control Formulation 4: Aqueous Solution, 0.1% Brassinolide

Formula composition: 80% of brassinolide technical grade (1.25 g), ethanol (co-solvent, 10 g), ethylene glycol (antifreeze, 30 g), water made up to 1 kg.

Preparation method: a homogeneous oil phase was made by mixing the brassinolide technical grade and alcohol. An aqueous phase was made by adding glycol into water; under high speed stirring, the oil phase was added to the aqueous phase to form a good aqueous solution containing 0.1% of the active ingredient. This product was coded as C4.

Control Formulation 5: Aqueous Solution, 0.01% Typhasterol

Formula composition: 80% of typhasterol technical grade (0.125 g), ethanol (co-solvent, 5 g), ethylene glycol (antifreeze, 30 g), water made up to 1 kg.

Preparation method: a homogeneous oil phase was made by mixing the typhasterol technical grade and alcohol. An aqueous phase was made by adding glycol into water; under high speed stirring, the oil phase was added to the aqueous phase to form a good aqueous solution containing 0.01% of the active ingredient. This product was coded as C5.

Control Formulation 6: Aqueous Solution, 0.1% Canola Pollen Extract

Formula composition: Canola pollen extract (1 g), NO 150 solvent oil (solvent, 10 g), polyoxyethylene styryl phenyl ether (emulsifier, 40 g), polypropylene alcohol (thickener, 70 g), diatomaceous earth (carrier, 20 g) and water made up to 1 kg Preparation method: a homogeneous oil phase was made by mixing the canola pollen extract, No 150 solvent oil and polyoxyethylene styrene phenyl ether. An aqueous phase was made by adding polypropylene alcohol, diatomaceous earth and water; under high speed stirring, the oil phase was added to the aqueous phase to form a good aqueous solution containing 0.1% of the active ingredient. This product was coded as C6.

Control Formulation 7: Soluble Powder, 1% Beewax Extract

Formula composition: Beeswax extract (10 g), alkyl naphthalene sulfonic acid formaldehyde condensate (dispersant, 6 g), alkylnaphthalene sulfonate (wetting agent, 10 g), soluble starch made up to 1 kg.

Preparation method: The components described above were thoroughly mixed, ground with a superfine grinding mill to obtain soluble powder containing 1% of the active ingredient. This product was coded as C7.

Control Formulation 8: Aqueous Solution, 0.1% 14-Hydroxylated Brassinosteroids

Formula composition: 80% of 14-hydroxylated brassinosteroids. (1.25 g), ethanol (co-solvent, 11 g), ethylene glycol (antifreeze, 25 g), water made up to 1 kg.

Preparation method: a homogeneous oil phase was made by mixing 14-hydroxylated brassinosteroid technical grade and ethanol. An aqueous phase was made by adding ethylene glycol and water. Under high speed stirring, the oil phase was added to the aqueous phase to form a good aqueous solution containing 0.01% of the active ingredient. This product was coded as C8.

Experimental examples 1-11 with compositions described above illustrated their applications against fungi-, bacteria- and/or virus-caused plant diseases.

Colby equation was used to calculate the expected control effect of two active ingredients of FZ and YC, $$\text{Expected control effect} = FZ + YC - (FZ*YC/100)$$

FZ=observed control effect of FZ at the same concentration of FZ in the composition YC=observed control effect of YC at the same concentration of YC in the composition Partial experimental methods were as follows:

Standard Test Method for Rice: pot assay was used. 12 pots were used for each group. Each group was divided into three treatments and a water blank control. Seven days prior to rice break period, whole rice plants were sprayed with the same volume of three treatment chemicals as that of water blank control until dripping. Twenty four hours after spraying, spore inoculation was conducted by spray inoculation. Six days after inoculation, spraying was repeated with water as a control, each treatment was repeated three times. Survey was conducted in rice maturity. The total number of rice plants and the number of diseased plants were recorded, and control was calculated.

Cucumber experimental methods: pot assay was used. 12 pots were used for each group. Each group was divided into three treatments and a water blank control. At 2-leaf stage, whole cucumber plants were treated by foliar spraying, with the same volume of three treatment chemicals as that of water blank control until dripping. Twenty four hour later, all plants were inoculated with spores by foliar spraying. After the onset of investigated disease in the blank control treatment, disease progression in all other treatments was investigated and control effects were calculated.

Orange Huanglongbing (Citrus HLB) Experimental Methods:

In greenhouse condition, developing citrus plants (e.g., orange) with HLB symptoms were transferred into black bugs with an irrigation condition. Four groups of leaves (10 leaves/group) were selected for each plant. There were sprayed with diluted water solution of the FZ, YC and their combination, and water blank, respectively. Five replicates were set up. Four sprayings were performed with a 7-day interval. After 1 month from the last spraying, DNA was extracted from treated leaves, titers pf HLP was determined with PCR kits. Citrus plant leaves treated with water dilution of FZ, YC and their combinations were considered as treatment groups. Citrus plant leaves treated with water was considered as a control group.

control effect=100%*(control group-treatment group)/control group

Experimental Example 1: Antimicrobial and Synergistic Experiment of the Composition of Rhubarb Extract and Brassinolide Against Cucumber Downy Mildew

TABLE 1 antimicrobial effect of individual components against cucumber downy mildew

| Product code | Component | Percent of AI | Dilution | Control effect (%) |
|---|---|---|---|---|
| C1 | Rhubarb extract | 3.0% | 600 | 60.5 |
| C4 | brassinolide | 0.1% | 25000 | 5.1 |

TABLE 2 antimicrobial effect of the composition against cucumber downy mildew

| Product code | Component | Percent of AI | Dilution | Expected control effect (%) | Experimental control effect (%) |
|---|---|---|---|---|---|
| A1 | Rhubarb extract | 0.4995% | 100 | 62.5 | 77.1 |
|  | 80% brassinolide | 0.0005% |  |  |  |

Experimental Example 2: Antimicrobial and Synergistic Experiment of the Composition of Giant Knotweed Extract and Typhasterol Against Rice Blast

TABLE 3 antimicrobial effect of individual components against rice blast

| Product code | Component | Percent of AI | Dilution | Control effect (%) |
|---|---|---|---|---|
| C2 | Giant knotweed extract | 5.0% | 1600 | 65.2 |
| C5 | typhasterol | 0.01% | 1600 | 20.3 |

TABLE 4 antimicrobial effect of the composition against rice blast

| Product code | Component | Percent of AI | Dilution | Expected control effect (%) | Experimental control effect (%) |
|---|---|---|---|---|---|
| A2 | Giant knotweed extract | 0.49875% | 1000 | 72.3 | 90.5 |
|  | 80% typhasterol | 0.0125% |  |  |  |

Experimental Example 3: Antimicrobial and Synergistic Experiment of the Composition of Giant Knotweed Extract and Canola Pollen Extract Against Eggplant *Phytophthora* Fruitrot

TABLE 5 antimicrobial effect of individual components against eggplant *Phytophthora* fruitrot

| Product code | Component | Percent of AI | Dilution | Control effect (%) |
|---|---|---|---|---|
| C2 | Giant knotweed extract | 5.0% | 1700 | 52.8 |
| C6 | Canola pollen extract | 0.1% | 32 | 7.9 |

TABLE 6 antimicrobial effect of the composition against eggplant *Phytophthora* fruitrot

| Product code | Component | Percent of AI | Dilution | Expected control effect (%) | Experimental control effect (%) |
|---|---|---|---|---|---|
| A3 | Giant knotweed extract | 7.5% | 2500 | 56.5 | 71.3 |
|  | Canola pollen extract | 7.5% |  |  |  |

Experimental Example 4: Antimicrobial and Synergistic Experiment of the Composition of *Cassia* Seed Extract and Beewax Extract Against Strawberry Root Rot

TABLE 7 antimicrobial effect of individual components against strawberry root rot

| Product code | Component | Percent of AI | Dilution | Control effect (%) |
|---|---|---|---|---|
| C3 | *Cassia* seed extract | 10% | 3300 | 61.3 |
| C7 | beewax extract | 1% | 70000 | 25.4 |

TABLE 8 antimicrobial effect of the composition against strawberry root rot

| Product code | Component | Percent of AI | Dilution | Expected control effect (%) | Experimental control effect (%) |
|---|---|---|---|---|---|
| A4 | *Cassia* seed extract | 4.48% | 1500 | 71.1 | 87.9 |
|  | beewax extract | 0.02% |  |  |  |

Experimental Example 5: Antimicrobial and Synergistic Experiment of the Composition of Giant Knotweed Extract and 14-Hydrolated Brassinosteroids Against Grape Downy Mildew

TABLE 9 antimicrobial effect of individual components against grape downy mildew

| Product code | Component | Percent of AI | Dilution | Control effect (%) |
|---|---|---|---|---|
| C2 | Giant knotweed extract | 5.0% | 1600 | 66.8 |
| C8 | 14-hydroxylated brassinosteroids | 0.1% | 96000 | 15.7 |

TABLE 10 antimicrobial effect of the composition against grape downy mildew

| Product code | Component | Percent of AI | Dilution | Expected control effect (%) | Experimental control effect (%) |
|---|---|---|---|---|---|
| A5 | Giant knotweed extract | 49.98% | 16000 | 72.0 | 89.6 |
|  | 80% 14-hydroxylated brassino-steroids | 0.02% |  |  |  |

Experimental Example 6: Antimicrobial and Synergistic Experiment of the Composition of Rhubarb Extract and Beewax Extract Against Tomato Leaf Curl Virus Disease

TABLE 11 antimicrobial effect of individual components against tomato leaf curl virus disease

| Product code | Component | Percent of AI | Dilution | Control effect (%) |
|---|---|---|---|---|
| C1 | rhubarb extract | 3.0% | 300 | 36.3 |
| C7 | Beewax extract | 1% | 35000 | 28.0 |

TABLE 12 antimicrobial effect of the composition against tomato leaf curl virus disease

| Product code | Component | Percent of AI | Dilution | Expected control effect (%) | Experimental control effect (%) |
|---|---|---|---|---|---|
| A6 | rhubarb extract | 19.95% | 2000 | 54.1 | 72.0 |
|  | Beewax extract | 0.05% |  |  |  |

Experimental Example 7: Antimicrobial and Synergistic Experiment of the Composition of *Cassia* Seed Extract and Canola Pollen Extract Against Potato Early Blight

TABLE 13 antimicrobial effect of individual components against potato early blight

| Product code | Component | Percent of AI | Dilution | Control effect (%) |
|---|---|---|---|---|
| C3 | Cassia seed extract | 10% | 2500 | 56.7 |
| C6 | Canola pollen extract | 0.1% | 150 | 10.2 |

TABLE 14 antimicrobial effect of the composition against potato early blight

| Product code | Component | Percent of AI | Dilution | Expected control effect (%) | Experimental control effect (%) |
|---|---|---|---|---|---|
| A7 | Cassia seed extract | 60% | 15000 | 61.1 | 74.7 |
|  | Canola pollen extract | 10% |  |  |  |

Experimental Example 8: Antimicrobial and Synergistic Experiment of the Composition of Rhubarb Extract and Beewax Extract Against Rose Powdery Mildew

TABLE 15 antimicrobial effect of individual components against rose powdery mildew

| Product code | Component | Percent of AI | Dilution | Control effect (%) |
|---|---|---|---|---|
| C1 | rhubarb extract | 3.0% | 600 | 79.1 |
| C7 | beewax extract | 1.0% | 9700 | 3.1 |

TABLE 16 antimicrobial effect of the composition against rose powdery mildew

| Product code | Component | Percent of AI | Dilution | Expected control effect (%) | Experimental control effect (%) |
|---|---|---|---|---|---|
| A8 | rhubarb extract | 78.4% | 15500 | 79.7 | 96.1 |
|  | beewax extract | 1.6% |  |  |  |

Experimental Example 9: Antimicrobial and Synergistic Experiment of the Composition of Giant Knotweed Extract and Beewax Extract Against Soybean Rust

TABLE 17 antimicrobial effect of individual components against soybean rust

| Product code | Component | Percent of AI | Dilution | Control effect (%) |
|---|---|---|---|---|
| C2 | Giant knotweed extract | 5.0% | 1550 | 67.4 |
| C7 | beewax extract | 1.0% | 70000 | 21.0 |

TABLE 18 antimicrobial effect of the composition against soybean rust

| Product code | Component | Percent of AI | Dilution | Expected control effect (%) | Experimental control effect (%) |
|---|---|---|---|---|---|
| A9 | Giant knotweed extract | 89.6% | 28000 | 74.2 | 91.6 |
|  | beewax extract | 0.4% |  |  |  |

Experimental Example 10: Antimicrobial and Synergistic Experiment of the Composition of Giant Knotweed Extract and Brassinolide Against Pepper Bacterial Wilt

TABLE 19 antimicrobial effect of individual components against pepper bacterial wilt

| Product code | Component | Percent of AI | Dilution | Control effect (%) |
|---|---|---|---|---|
| C2 | Giant knotweed extract | 5.0% | 26.3 | 43.9 |
| C4 | brassinolide | 0.1% | 658 | 11.7 |

TABLE 20 antimicrobial effect of the composition against pepper bacterial wilt

| Product code | Component | Percent of AI | Dilution | Expected control effect (%) | Experimental control effect (%) |
|---|---|---|---|---|---|
| A10 | Giant knotweed extract | 94.905% | 500 | 50.5 | 68.8 |
|  | 80% brassinolide | 0.095% |  |  |  |

Experimental Example 11: Antimicrobial and Synergistic Experiment of the Composition of Giant Knotweed Extract and Beewax Extract Against Citrus Huanglongbing

TABLE 21 antimicrobial effect of individual components against citrus Huanglongbing

| Product code | Component | Percent of AI | Dilution | Control effect (%) |
|---|---|---|---|---|
| C2 | Giant knotweed extract | 5.0% | 2000 | 6.7 |
| C7 | Beewax extract | 1.0% | 36.3 | 54.1 |

TABLE 22 antimicrobial effect of the composition against citrus Huanglongbing

| Product code | Component | Percent of AI | Dilution | Expected control effect (%) | Experimental control effect (%) |
|---|---|---|---|---|---|
| A11 | Giant knotweed extract | 2.5% | 1000 | 57.2 | 74.0 |
|  | Beewax extract | 27.5% |  |  |  |

Experimental examples (1-11) demonstrated that an obvious synergistic effect was observed for compositions of between FZ and YC within an appropriate ratio. When compared with individual components, compositions of FZ and YC significantly improved the control effect of plant diseases, therefore, reducing the amount of individual components, reducing farmers' expenses and also decreasing the impact on environment. In addition, the compositions of FZ and YC showed good efficacy against a variety of diseases on various crops, and their compositions displayed a broad antimicrobial spectrum.

What is claimed is:

1. A phytochemical composition exhibiting antimicrobial effects comprising:
   a carrier; and
   a synergistic combination of active ingredients consisting essentially of a first active ingredient (FZ) and a second active ingredient (YC), wherein
   a) FZ includes:
      1) rhubarb extract;
      2) giant knotweed extract;
      3) cassia seed extract; or
      4) combinations thereof; and wherein
   b) YC includes:
      1) canola pollen extract;
      2) beewax extract;
      3) synthesized brassinosteroid; or
      4) combinations thereof.

2. The composition according to claim 1, wherein the FZ is selected from giant knotweed extract and cassia seed extract.

3. The composition according to claim 1, wherein the FZ is selected from giant knotweed extract.

4. The composition according to claim 1, wherein the YC is selected from Canola pollen extract, beewax extract, and synthesized brassinosteroid.

5. The composition according to claim 1, wherein the YC is selected from beewax extract.

6. The composition according to claim 1, wherein the percent content of FZ in the composition is 0.001-99.0% (w/w), and percent content of YC in the composition is 0.000001-60% (w/w).

7. The composition according to claim 6, wherein the percent content of FZ and YC in the composition is 0.01-60% (w/w) and 0.00001-40% (w/w), respectively.

8. The composition according to claim 1, wherein the weight ratio between FZ and YC (FZ:YC) is from 0.0001:1 to 1000000:1.

9. The composition according to claim 8, wherein the weight ratio between FZ and YC (FZ:YC) is from 0.001:1 to 100000:1.

10. The composition according to claim 9, wherein the weight ratio between FZ and YC (FZ:YC) is from 0.01:1 to 10000:1.

11. The composition according to claim 10, wherein the application concentration ratio between FZ and YC (FZ:YC) is from 1000 ppm:0.001 ppm to 1 ppm:500 ppm.

12. The composition according to claim 11 is from 500 ppm:0.01 ppm to 5 ppm:200 ppm.

13. The composition according to claim 1, where the composition is formulated as any one of the following formulation types: emulsifiable concentrate (EC), aqueous emulsion (EW), microemulison (ME), suspension concentrate (SC), oil dispersion (OD), capsule suspension (CS), wettable powder (WP), water dispersible granule (WDG). Soluble powder (SP), soluble granule (SG), suspension emulsion (SE), flowable concentrate for seed treatment (FS), aqueous solution (AS) and ready to use formulation.

14. The composition of claim 1, wherein
   the one or more rhubarb extracts include anthraquinones such as rhein, aloe-emodin, emodin, physcion, chrysophanol, physcion-glucoside, chrysophanol-glucoside, emodin-glucoside and rhein-glucoside;
   the one or more giant knotweed extracts, include anthraquinones such as emodin, physcion, chrysophenol, emodin-glucoside, physcion-glucosde, chrysophanol-glucoside and resveratrol;
   the one or more cassia seed extracts include anthraquinones such as emodin, chrysophanolphyscion, obtusin, obtusifolin and their corresponding glucosides;
   the one or more canola pollen extracts include brassinosteroids, such as brassinolide. 24-epibrassinolide, 28-epihomobrassinolidem, 28-homobrassinolide, dolicholide. typhasterol, 28-norcastasterone and 22, 23, 24-trisepibrassinolide; and
   the one or more beewax extracts, include brassinosteroids, such as brassinolide, 24-epibrassinolide, 28-epihomobrassinolidem, 28-homobrassinolide, dolicholide. typhasterol, 28-norcastasterone and 14-hydroxylated brassinosteroid; and
   the one or more synthesized brassinosteroids include one or more of brassinolide. 24-epibrassinolide, 28-epihomobrassinolidem, 28-homobrassinolide and typhasterol.

15. The composition of claim 1, wherein said combination has a synergistic antimicrobial effect.

16. A method for protecting a plant from diseases caused by fungi, bacteria or virus, comprising applying to the plant the composition of claim 1, thereby inducing plant resistance, promoting plant growth and/or enhancing plant yields.

17. The method of claim 16, wherein the plant is selected from the group consisting of: cucumber, pumpkin, squash, tomato, onion, shallots, beet, pepper, wheat, cereals, rice, sunflower, green bean, tobacco, flax, strawberry, grape, citrus, pears, apple, peony, chrysanthemum, rose and the plant diseases caused by fungi, bacteria, or virus is optionally: powdery mildew, downy mildew, late blight, pythium, damping-off disease, canker, black shank disease, Canker, early blight, rice blast, sheath blight, black scab, rust, glume spot disease, net blotch, leaf blight, botrytis disease, blast blight, bacterial wilt disease, bacterial stem rot disease and/or citrus huanglongbing.

18. The method of claim 17, wherein the plant is protected from cucumber and grape downy mildew and powdery mildew; cucumber and strawberry botrytis disease; citrus huanglongbing, rice blast; rice sheath blight and rice bacterial blight; peanut, pepper and tomato bacterial wilt; sunflower bacterial stem rot; and pear scab.

* * * * *